(12) United States Patent
Goodman

(10) Patent No.: US 11,583,405 B2
(45) Date of Patent: *Feb. 21, 2023

(54) HARD SUBSTANCE MULTI-HOODED ENARTHRODIAL JOINT IMPLANT

(71) Applicant: Floyd G. Goodman, Williamston, MI (US)

(72) Inventor: Floyd G. Goodman, Williamston, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/974,184

(22) Filed: Nov. 4, 2020

(65) Prior Publication Data

US 2021/0059823 A1  Mar. 4, 2021

Related U.S. Application Data

(63) Continuation-in-part of application No. 15/932,520, filed on Mar. 10, 2018, now Pat. No. 10,849,759.
(Continued)

(51) Int. Cl.
*A61F 2/34* (2006.01)
*A61F 2/42* (2006.01)
*A61F 2/40* (2006.01)

(52) U.S. Cl.
CPC .............. *A61F 2/34* (2013.01); *A61F 2/4081* (2013.01); *A61F 2/4241* (2013.01);
(Continued)

(58) Field of Classification Search
CPC .. A61F 2/32; A61F 2/34; A61F 2/3601; A61F 2/4081; A61F 2/30448;
(Continued)

(56) References Cited

U.S. PATENT DOCUMENTS 5,462,575 A  10/1995  Del Corso
5,624,464 A  4/1997  Wagner et al.
(Continued)

OTHER PUBLICATIONS

Goodman, Floyd G., U.S. Appl. No. 62/601,178, filed Mar. 13, 2017 A.D., "Ceramic Multi-Hooded Enarthrodial Joint Implant."
(Continued)

*Primary Examiner* — Alvin J Stewart
(74) *Attorney, Agent, or Firm* — Christopher John Rudy

(57) ABSTRACT

Multi-hooded enarthrodial joint implant has a hard substance articulating cup including a hard substance head-receiving cup having an articular surface upon which a head of a joint can articulate, and which, in general, has a margin generally about a hemisphere more or less and at least two hoods that are marginally extended continuations of superior one-half or so of cup containment of a sufficient magnitude to reduce an overall dimension of socket outlet to less than a hemisphere, which can embrace and contain the head. The head is made of a hard substance and has a truncated generally circular cross section, a truncated surface with a feature for attachment of the stem, and an opposing articular surface for articulation against the articular surface of the ceramic head-receiving cup. As an ensemble, the cup is combined with the head, typically with a stem, for a total joint implant. The hard substance may be, for example, a composite substance, a metal or a metal alloy. Either the cup or the head, but not both, may be ceramic when employed in an ensemble.

30 Claims, 4 Drawing Sheets

Related U.S. Application Data

(60) Provisional application No. 62/601,178, filed on Mar. 13, 2017.

(52) U.S. Cl.
CPC ............... *A61F 2002/3429* (2013.01); *A61F 2002/3482* (2013.01); *A61F 2002/4085* (2013.01); *A61F 2002/4253* (2013.01)

(58) Field of Classification Search
CPC .... A61F 2002/30578; A61F 2002/3233; A61F 2002/3241; A61F 2/4241; A61F 2002/3429; A61F 2002/3482; A61F 2002/4085
See application file for complete search history.

(56) References Cited

U.S. PATENT DOCUMENTS

| | | | |
|---|---|---|---|
| 5,725,591 A * | 3/1998 | DeCarlo, Jr. | A61F 2/4637 623/22.29 |
| 5,871,547 A | 2/1999 | Abouaf et al. | |
| 6,093,208 A | 7/2000 | Tian | |
| 6,096,083 A | 8/2000 | Keller et al. | |
| 6,129,765 A * | 10/2000 | Lopez | A61F 2/468 623/22.15 |
| 6,290,727 B1 * | 9/2001 | Otto | A61F 2/30724 623/22.21 |
| 6,299,647 B1 | 10/2001 | Townley | |
| 6,319,285 B1 | 11/2001 | Chamier et al. | |
| 6,682,567 B1 | 1/2004 | Schroeder | |
| 6,881,229 B2 | 4/2005 | Khandkar et al. | |
| 7,335,231 B2 | 2/2008 | McLean | |
| 7,455,694 B2 | 11/2008 | Epaules et al. | |
| 7,520,902 B2 * | 4/2009 | Deloge | A61F 2/32 623/22.15 |
| 7,682,398 B2 | 3/2010 | Croxton et al. | |
| 7,695,521 B2 | 4/2010 | Ely et al. | |
| 7,780,739 B2 * | 8/2010 | Lakin | A61F 2/32 623/22.17 |
| 7,892,289 B2 | 2/2011 | Serafin, Jr. et al. | |
| 7,981,160 B1 * | 7/2011 | Serafin, Jr. | A61F 2/34 623/22.25 |
| 8,679,187 B2 | 3/2014 | Allen et al. | |
| 8,801,797 B2 | 8/2014 | Imhof | |
| 8,834,576 B1 | 9/2014 | Serafin, Jr. | |
| 9,078,754 B1 | 7/2015 | Serafin, Jr. et al. | |
| 9,173,740 B2 | 11/2015 | Gradel | |
| 9,259,508 B2 | 2/2016 | Serafin, Jr. et al. | |
| 9,272,095 B2 | 3/2016 | Felts et al. | |
| 9,308,674 B1 | 4/2016 | Serafin, Jr. et al. | |
| 9,427,322 B1 | 8/2016 | Serafin, Jr. | |
| 9,561,111 B1 | 2/2017 | Goodman | |
| 9,907,661 B2 | 3/2018 | Ries | |
| 10,849,759 B2 * | 12/2020 | Goodman | A61F 2/4081 |
| 2002/0013625 A1 | 1/2002 | Abouaf et al. | |
| 2002/0031675 A1 | 3/2002 | Cales et al. | |
| 2002/0116068 A1 | 8/2002 | McLean | |
| 2003/0171817 A1 | 9/2003 | Rambert et al. | |
| 2003/0216732 A1 | 11/2003 | Truckai et al. | |
| 2007/0191961 A1 | 8/2007 | Aux Epaules et al. | |
| 2008/0074643 A1 | 3/2008 | Chen et al. | |
| 2009/0093887 A1 | 4/2009 | Walter et al. | |
| 2010/0076566 A1 | 3/2010 | Serafin, Jr. et al. | |
| 2010/0087930 A1 | 4/2010 | Tuke et al. | |
| 2011/0243650 A1 | 10/2011 | Linares | |
| 2011/0257757 A1 | 10/2011 | Popoola et al. | |
| 2012/0252709 A1 | 10/2012 | Felts et al. | |
| 2013/0261761 A1 | 10/2013 | Whitaker et al. | |
| 2014/0069202 A1 | 3/2014 | Fisk | |
| 2014/0128988 A1 | 5/2014 | Muratoglu et al. | |
| 2017/0202671 A1 | 7/2017 | Ries | |

OTHER PUBLICATIONS

Goodman, Floyd G., U.S. Appl. No. 15/932,520, filed Mar. 10, 2018 A.D., "Ceramic Multi-Hooded Enarthrodial Joint Implant."
Nielsen, Eric M., Reply and Amendment with Claims and Remarks filed on Oct. 27, 2017 A.D., in Ries, U.S. Appl. No. 15/282,738.
Watkins, Marcia Lynn, Office action dated Aug. 1, 2017 A.D., in Ries, U.S. Appl. No. 15/282,738.
Stryker Howmedica Osteonlcs, "Wear Rate Comparison," ca. 1990-2003, Lit. No. LWRC-TC 500 11/03 MC/GS.

\* cited by examiner

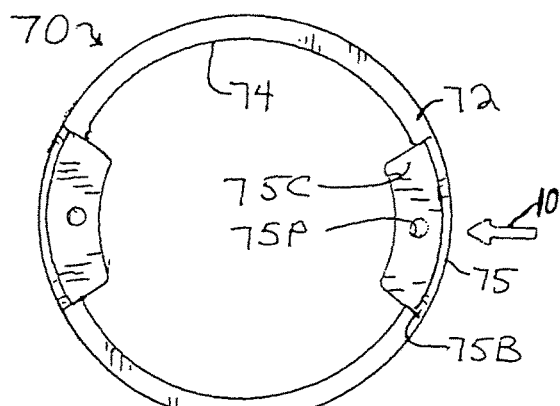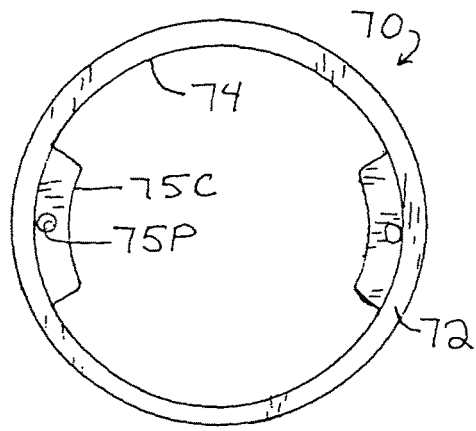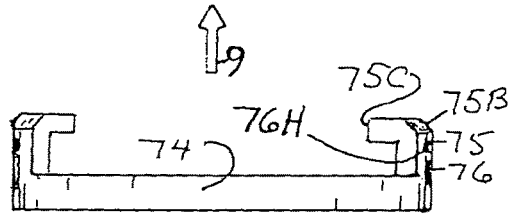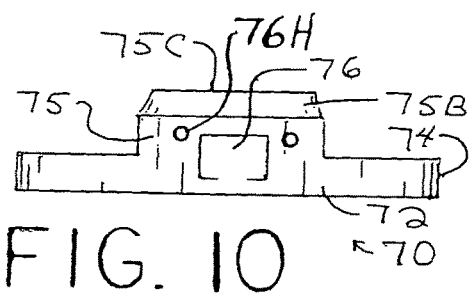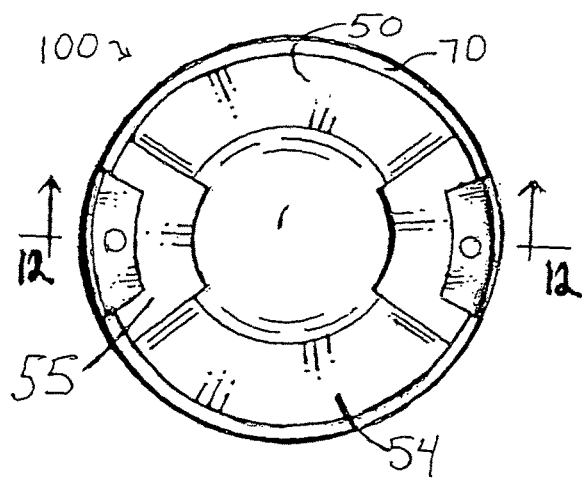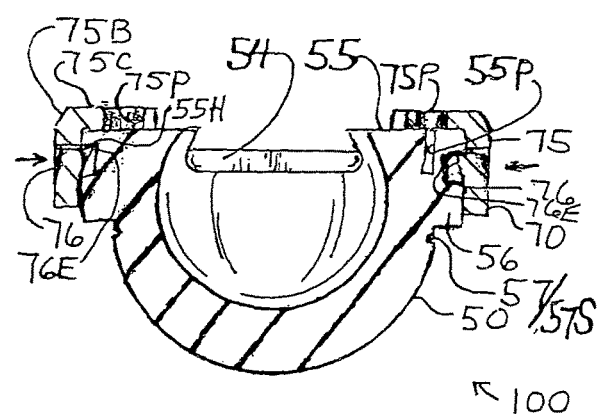

HARD SUBSTANCE MULTI-HOODED ENARTHRODIAL JOINT IMPLANT

This claims benefits under 35 USC 120 as a continuation-in-part of parent nonprovisional utility patent application No. U.S. Ser. No. 15/932,520 filed on Mar. 10, 2018 A.D., now patent No. U.S. Pat. No. 10,849,759 B2, which, as does this through the '520 parent application, claims the benefits under 35 USC 119(e) of provisional patent application No. U.S. 62/601,178 filed on Mar. 13, 2017 A. D. The specifications of those two earlier applications, to include their drawings, are incorporated herein by reference in their entireties.

FIELD AND PURVIEW OF THE INVENTION

This concerns a multi-hooded enarthrodial joint implant with a hard surface articulating cup and/or head, separately, as an ensemble or kit, or part thereof. For example, the implant may be an ensemble for a hip or shoulder with a double-hooded acetabular or glenoid cup and a modular femoral or humeral stem with truncated ball head of matching or complimentary metal.

BACKGROUND TO THE INVENTION

Various enarthrodial joint implants are known. Among those, some have two or more "hoods," also known as "veils," on a portion of an articulating cup for ameliorating dislocation of an inserted ball of the joint. See, e.g., Serafin, Jr. et al., patent No. U.S. Pat. No. 7,981,160 B1. The acetabular cup of that implant is fitted with a suitably resilient, tough material that may include a plastic such as a polyurethane or polyolefin and so forth, for example, a polyethylene, say, an ultra high molecular weight polyethylene (UHMWPE). In order to assist in retaining the ball head of the femoral component in the cup, a securing member provides for resistance against outward displacement of hoods of the cup. A drawback may ensue with employment of such materials as UHMWPE or other resilient materials for the cup in that, when implanted, they may leave wear debris that may engender osteolytic loosening of the implant. In address of plastic wear debris, some enarthrodial joint art employs as a wear couple a hard-surface-on hard-surface articulation such as a metal-on-metal, metal-on-ceramic, or ceramic-on-ceramic articulation. Such rigid, hard materials, however, are substantially inflexible, which may be considered a drawback. Thus, hard enarthrodial joint wear couples typically are limited to configurations unconstrained from dislocation save that provided by healthy tissue, which may not be present about a surgical implant site; or, if constrained from dislocation, are constrained with implant structures that are bulky, cumbersome or complex mechanically, or limit more full and natural range of motion, with some of these retaining a plastic cup such as of UHMWPE. Implants, then, are made with various materials, and some implants are coated, notably with porous or other bone-ingrowth engendering coatings. See, Del Corso, U.S. Pat. No. 5,462,575; Abouaf et al., U.S. Pat. No. 5,871,547; Tian, U.S. Pat. No. 6,093,208; Keller et al., U.S. Pat. No. 6,096,083; Townley, U.S. Pat. No. 6,299,647 B1; Chamier et al., U.S. Pat. No. 6,319,285 B1; Schroeder, U.S. Pat. No. 6,682,567 B1; Khandkar et al., U.S. Pat. No. 6,881,229 B2; McLean, U.S. Pat. No. 7,335,231 B2; Epaules et al., U.S. Pat. No. 7,455,694 B2; Croxton et al., U.S. Pat. No. 7,682,398 B2; Ely et al., U.S. Pat. No. 7,695,521 B2; Lakin et al., U.S. Pat. No. 7,780,739 B2; Serafin, Jr. et al., U.S. Pat. No. 7,892,289 B2; Allen et al., U.S. Pat. No. 8,679,187 B2; Imhof, U.S. Pat. No. 8,801,797 B2; Serafin, Jr., U.S. Pat. No. 8,834,576 B1; Serafin, Jr. et al., U.S. Pat. No. 9,078,754 B1; Gradel, U.S. Pat. No. 9,173,740 B2; Serafin, Jr. et al., U.S. Pat. No. 9,259,508 B2; Serafin, Jr. et al., U.S. Pat. No. 9,308,674 B1; Serafin, Jr., U.S. Pat. No. 9,427,322 B1; Goodman, U.S. Pat. No. 9,561,111 B1; Abouaf et al., Pub. No. US 2002/0013625 A1; Cales et al., Pub. No. US 2002/0031675 A1; Walter et al., Pub. No. US 2009/0093887 A1; Serafin, Jr. et al., Pub. No. US 2010/0076566 A1; Tuke et al., Pub. No. US 2010/0087930 A1. See also, Ries, Pub. No. US 2017/0202671 A1.

It would be desirable to improve upon the art and/or provide it with an alternative. It would be desirable to provide an enarthrodial joint implant that ameliorates or solves one or more drawbacks in the art such as dislocation, breakage, and so forth.

A FULL DISCLOSURE OF THE INVENTION

Provided hereby is a multi-hooded enarthrodial joint implant with a hard substance articulating cup comprising a hard substance head-receiving cup having an articular surface upon which a head of a joint can articulate, and which, in general, has a margin generally about a hemisphere more or less and at least two hoods that are marginally extended continuations of superior one-half or so of cup containment of a sufficient magnitude to reduce an overall dimension of socket outlet to less than a hemisphere, which can embrace and contain the head. In an ensemble, the cup is combined with a modular head and stem arrangement for a total joint implant, in which the head is of a hard substance, the same or different from that of the cup, and has a truncated generally (i.e., of reasonable inclusion) circular cross section, a truncated surface with a feature for attachment of the stem, and an opposing articular surface for articulation against the articular surface of the hard surface head-receiving cup. Generally, in such an ensemble, at least one of the cup or the head is not made of ceramic. The head may be or contain a sphere, spheroid, ellipsoid, truncated rod, and so forth and the like element, at least in substantial part. Optionally provided can be a securing member that provides for resistance against any likelihood, if any, of cracking, fracture, or other failure of the hard substance such as by an application of unusually great outwardly displacing force. Additional optional feature(s) may be provided also such as a bone-interfacing coating; a ring, which may include, for example, a bone-interfacing coating; an outer backing shell for the cup; and so forth.

The invention is useful in arthroplasty.

Significantly, by the invention, problems in the art are ameliorated if not overcome. In particular, total joint implants are made dramatically more secure by resistance to dislocation and breakage, and even in a number of cases a reduction in wear debris, which may reduce a propensity for osteolytic loosening of the implant. Also, certain allergic reactions and/or potential for particulate reactivity may be reduced or avoided.

Numerous further advantages attend the invention.

The drawings form part of the specification hereof. With respect to the drawings, which are not necessarily drawn to scale and in which the lining of materials in sectional views, in general, is intended to be set forth generically for the materials that are employed herein—such as, for example, a composite, metal or metal alloy substance, but may include a ceramic head or cup, but not both, in an ensemble—the following is briefly noted:

FIG. 7 is a "front" view of a securing member of the invention for an ensemble therewith, the same able to be embodied as a 6-4 ELI titanium alloy ring.

FIG. 8 is a "rear" view of the securing member of FIG. 7.

FIG. 9 is a "side" view of the securing member of FIG. 7, taken along arrow 9 in FIG. 7.

FIG. 10 is a "side" view of the securing member of FIG. 7, taken along arrow 10, which is normal to arrow 9 in FIG. 7.

FIG. 11 is a "top" view of an ensemble of the invention, which includes the cup of FIG. 1 and the securing ring of FIG. 7, without security enhancing fasteners such as screws depicted for the sake of clarity.

FIG. 12 is a sectional view of the ensemble of FIG. 11, taken along 12-12 in FIG. 11.

Figure 1:
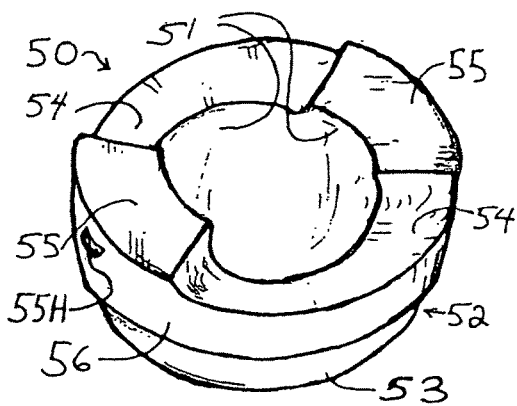
FIG. 1 is a perspective view of a hard substance multi-hooded enarthrodial joint implant cup of the invention for an ensemble therewith, the same being embodied as a double-hooded hard substance acetabular cup for a total conventional hip replacement implant.
Figure 2:
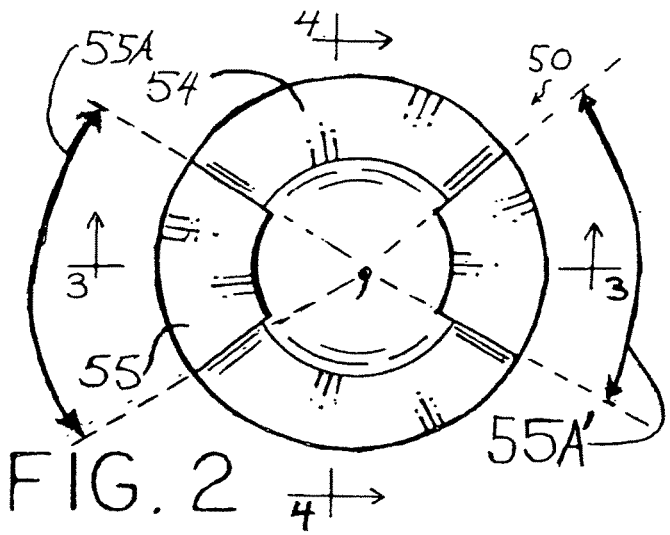
FIG. 2 is a "front" view of the cup of FIG. 1.
Figure 3:
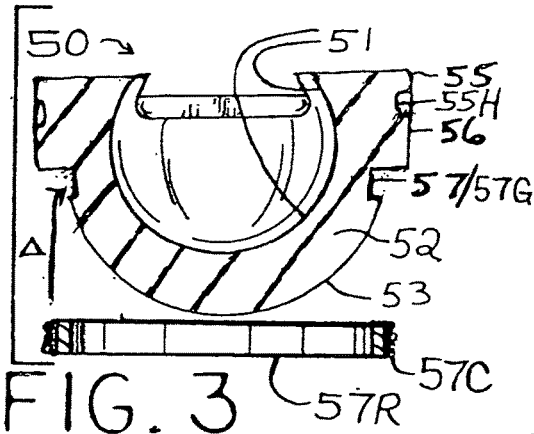
FIG. 3 is a sectional view of the cup of FIG. 1, taken along 3-3 of FIG. 2.
Figure 4:
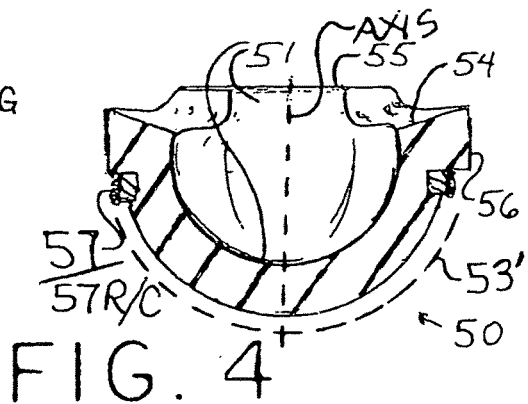
FIG. 4 is a sectional view of the cup of FIG. 1, taken along 4-4 of FIG. 2, which is normal to 3-3 of FIG. 2.

The invention can be further understood by the following additional detail, which, as with the foregoing, may be read in view of the drawings. Such is to be taken in an illustrative and not necessarily limiting sense.

The principles of the invention can be applied to provide a hard substance multi-hooded enarthrodial joint implant cup ensemble, or parts thereof, for any suitable enarthrodial joint, or other generally corresponding pivoting joint, to include the hip, shoulder, thumb or finger. The hip and shoulder are illustratively depicted.

Any suitable material may be employed. Generally, materials are biocompatible. It may be the case that the hard substance is not ceramic. Thus, material for the cup and any corresponding modular head for receipt in the cup may be selected from any suitable rigid, hard substance, to include any suitably rigid, strong materials that may include such plastics as nylons, polycarbonates or epoxies; composites; such metals as titanium or cobalt; and such metal alloys as stainless steel, titanium-vanadium-aluminum, cobalt-chrome, a cobalt-chromium-molybdenum alloy, and so forth. Additional component parts, if present, are made of suitable materials. For example, a backing shell or other part may be made of a suitable composite, metal, or metal alloy such as aforesaid, for example, a 6-4 ELI titanium alloy; a stem for the modular head and stem assembly may be made of a suitable composite, metal, or metal alloy, for example, a cobalt-chrome alloy, stainless steel, and so forth. If not metal, the hard substance can have hardness properties of or, akin to metal or ceramic. If ceramic is employed, say, as a cup or its corresponding head, and sometimes both under certain conditions, in a joint implant ensemble or as a component therefor, it may be any suitable ceramic, for instance, a ceramic such as an alumina. silicon nitride ceramic. or a zirconia, for example, MgO-TTZ such as in Serafin, Jr. et al., patent No. U.S. Pat. No. 9,259,508 B2. As to ceramics. in light of the parent application, the first and second hard substances of a cup and corresponding head may be the same as or different from the other, with, at least one of the first, and second hard substances being as follows:

in all enarthrodial joint applications, alumina, a silicon nitride ceramic, or a zirconia ceramic other than MgO-TTZ: or provided that the device is an enarthrodial joint component or ensemble other than for a hip, MgO-TTZ.

The hoods of the cup embrace the head of a joint greater than the circular cross section, for example, as a truncated spherical ball head greater than a hemisphere, in general, at least about their areas of contact with the head. Thus, in general, the hoods are marginally extended continuations of the superior one-half or so of the cup containment of a sufficient magnitude to reduce the overall dimension of the socket outlet to less than a half a circle in cross section, say again, a hemisphere in the case of a truncated spherical ball head. The truncated head is slid sideways into the cup into the embrace of the hoods. After insertion of the head into the hooded cup, the head is rotated in relation to the cup so as to bring its truncated surface into position to have the corresponding stem attached. Then any securing member may be brought into position.

More than one hood is required in the practice of the present invention. Thus, for instance, two, three, four or more hoods may be employed, say, with two opposing hoods; with three hoods equidistant about the margin of the cup and margin segments and hoods having about the same arc lengths, or with hoods having less of an arc length than the margins such as from about ½ to ¾ of the are length of the margins; with three hoods not equidistant about the margin and themselves having the same arc lengths, or with one having a larger arc length opposed by two with lesser arc lengths; with four hoods equidistant about the margin and margin segments and hoods having about the same arc lengths, or with hoods having less of an arc length than the margins; with four hoods about the margin, two of the hoods in a set opposing two of the hoods in another set with greater margins between the two sets of hoods than between each hood in a set, or in an asymmetric arrangement, and so forth. Advantageously, the hard substance multi-hooded enarthrodial joint implant is embodied as a double-hooded cup, which may be present without the securing member.

Any suitable configuration for the modular head and stem may be employed. In general, however, there is a head component separate from but attachable with a stem component. The attachment may be carried out by any suitable method or means such as one or more of gluing, screwing, friction fitting, pressure fitting, and so forth. A tapered receptacle into which a corresponding trunnion is inserted may be employed. For example, the head may contain the tapered receptacle, for example, a conically or frustoconically tapered receptacle, with the corresponding trunnion being provided on a stem extremity. A self-locking taper such as, for example, a Morse taper, may be employed.

As optional further securement, the securing member provides for resistance against any likelihood, if any, of cracking, fracture, or other failure of the ceramic such as by an application of unusually great outwardly displacing force. Preferably, the securing member secures at least two hoods, and may secure each of the hoods present with the cup. The securing member may take any suitable form, including that of a ring or a U-shaped or a horseshoe-shaped member.

Additional parts or components may be present. For instance, a backing shell may be present, into which the cup is inserted, or an implant bone insert such as in Serafin, Jr. et al., U.S. Pat. No. 7,892,289 B2, may be provided to the head.

With respect to the drawings, hard substance joint head 20 articulates within multi-hooded enarthrodial joint implant cup 50 in ensemble 100. Securing member 70 may be present.

The joint head 20—made, for example, of a composite such as a fiber reinforced polymer composite, which may be a carbon fiber-polycarbonate, a carbon fiber-polysulfone, a carbon fiber-polyetherketone, a polyaramid fiber-polycarbonate, a polyaramid fiber-polysulfone, or a polyaramid fiber-polyetherketone, and so forth and the like, or of a cobalt-chrome alloy, desirably a cobalt-chrome-molybdenum alloy, which may be a forged alloy of cobalt-chromium to ASTM F-799 specifications, or of a non-magnetic cobalt-chromium-molybdenum alloy as a wrought powder metallurgy product such as BioDur® CCM Plus alloy (Carpenter Technology Corp.), U.S. Pat. No. 5,462,575, or which may be made to another specification such as ASTM F1537 or ASTM F75, or a stainless steel, and so forth and the like, or perhaps a ceramic when configured in an ensemble with a cup 50 that is not a ceramic—is in a shape of a truncated sphere; has articulation surface 20A, blind frustoconical hole 20H with Morse taper in truncated surface 20S and central truncation distance 20T greater than the head radius, say, about from 60%, 65% or 70% to 75%, 80% or 85% of the head diameter; and is connectable to stem 21. For instance, the stem 21, which may be made of a material that the joint head 20 is made or of a different material selected from the above or of another substance, includes trunnion 21T having corresponding Morse taper, which is inserted into the hole 20H of the head 20 for insertion into the medullary canal of the resected upper femur of a human patient.

Figure 5:
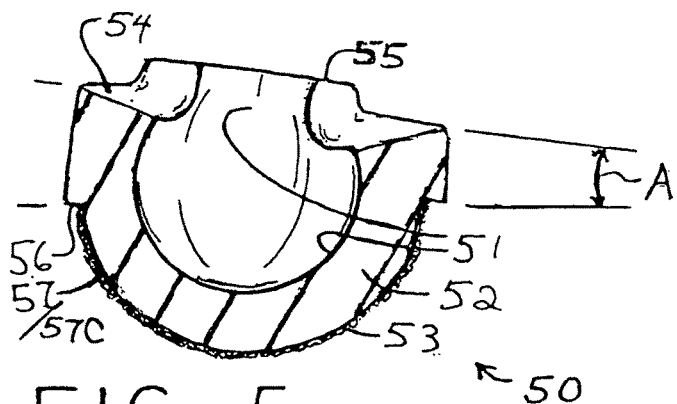
FIG. 5 is a sectional view of another hard substance multi-hooded enarthrodial joint implant cup of the invention for an ensemble therewith, the same being embodied as a double-hooded hard substance acetabular cup for a total conventional hip replacement implant, and having angular displacement of the margin and hoods. Compare, FIG. 4.
Figure 6:
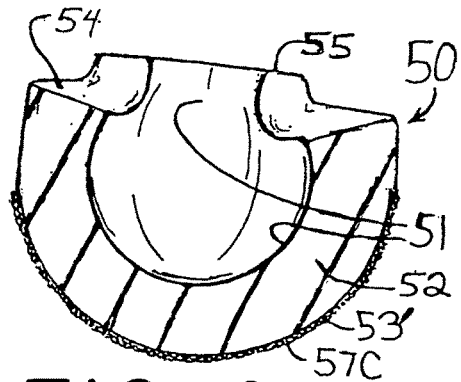
FIG. 6 is a sectional view of another hard substance multi-hooded enarthrodial joint implant cup of the invention for an ensemble therewith, embodied as a double-hooded hard substance acetabular cup for a total conventional hip replacement implant, and having angular displacement of the margin and hoods. Compare, FIG. 5.
Figure 13:
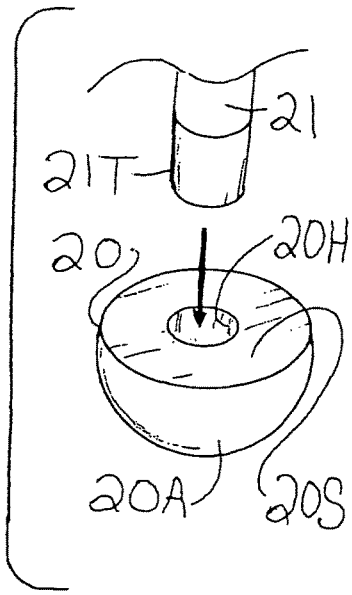
FIG. 13 is an exploded, perspective view of a modular head and stem arrangement for a total joint implant of the invention.
Figure 14:
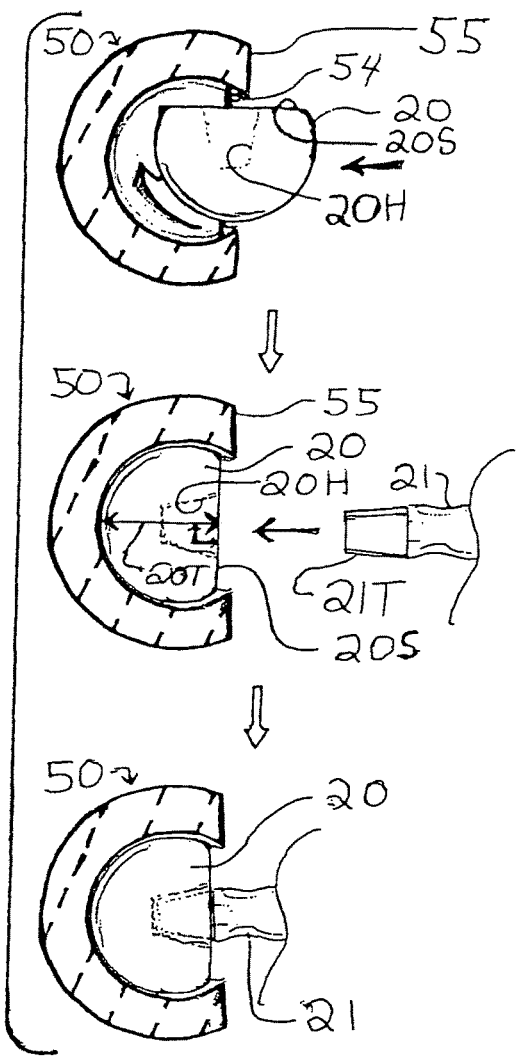
FIG. 14 is a schematic view of another hard substance multi-hooded enarthrodial joint implant cup with a modular head and stem arrangement for a total hip joint implant ensemble of the invention, and its assembly.
Figure 15:
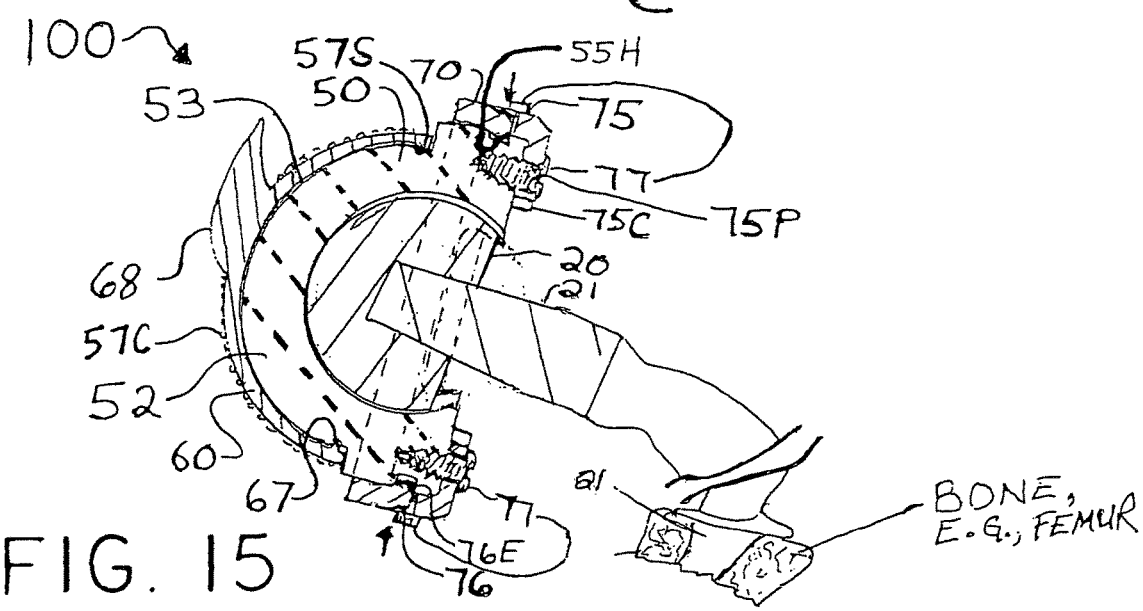
FIG. 15 is a sectional plan view of an ensemble such as that of FIG. 11 and as would be taken along 12-12 in FIG. 11, by which is embraced a ball head of a corresponding implant, here, the ball head of a femoral component for the total hip implant, with a modular head and stem arrangement such as illustratively depicted within FIGS. 13 and 14, two security enhancing fasteners, and a backing shell.
Figure 16:
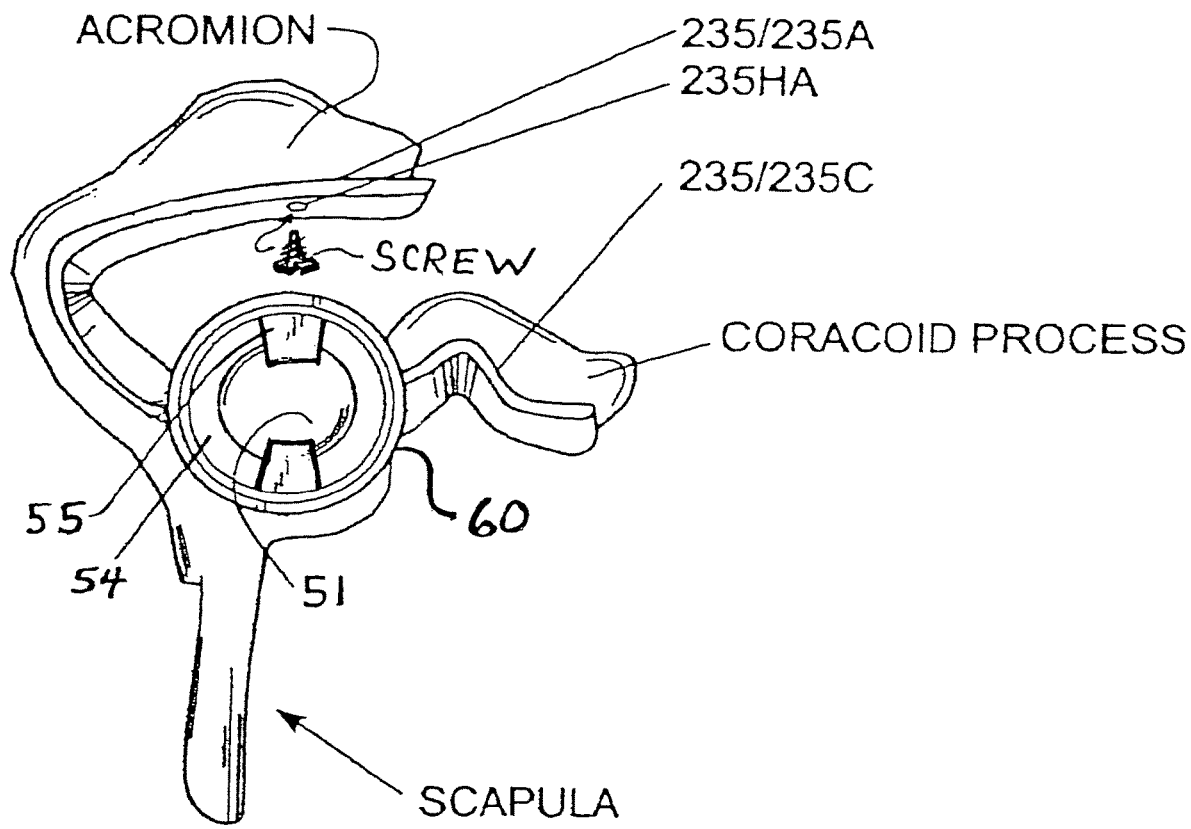
FIG. 16 is "front" view of a another hard substance multi-hooded enarthrodial joint implant cup with a modular head and stem arrangement for a shoulder joint implant of the invention.

The cup 50 made of a hard substance such as may be employed for the head 20—for example, a suitable composite, metal or metal alloy to include as exemplified as aforesaid, or perhaps a ceramic when configured in an ensemble with a head 20 that is not a ceramic—includes articular surface 51; body 52; back 53, which may be for facing a backing shell interior when inserted into backing shell 60, or back 53', which is for interfacing resected bone when implanted into the patient; margins 54; and hoods 55, which may have arcs, for example, arc 55A of about sixty-five degrees and arc 55A' of about seventy degrees, one or more of which may be provided in advance or at the surgical site with ring tab registering side hole 55H and/or pilot hole 55P. The cup 50 may also include circumferential lip 56, which is essentially or to a great extent flat, being essentially or to a great extent parallel with a central axis, and which, with the margins 54 and/or hoods 55, may be level (FIGS. 1-4, 11, 12, 15); be angled at angle "A," say, about from five to twenty degrees, for example, about ten degrees (FIGS. 5, 6); or be absent, wholly or essentially (FIG. 14). The cup 50 may also include fastening aid 57 such as porous coating 57C; circumferential groove 57G into which circumferential ring 57R may be positioned such as by heating to expand the ring 57R, positioning it over and then cooling it to shrink into the groove 57G such as found in Serafin, Jr. et al., U.S. Pat. No. 9,308,674 B1, with the ring 57R able to carry a supply of porous coating 57C; and circumferential slot 57S for engagement through auspices of a locking ring with the backing shell 60 made, for example, of 6-4 ELI titanium alloy per ASTM F-136 specifications, which has complimentary fastening aid 67, here, a circumferential protrusion. The backing shell 60 also may have, among other things, optional cox-comb 68 for insertion into bone stock, notably in the case of a total hip joint replacement implant, and/or have a roughened or the porous coated surface 57C for interfacing with resected bone surface and promoting bone ingrowth to stabilize the implant. A backing shell 60 for the shoulder may also have arm(s) 235 such as first arm 235A for fastening to the acromion, which may be assisted by providing hole 235HA for a bone screw, and/or second arm 235C for fastening to the coracoid process. Surgical cement such as polymethylmethacrylate may be used.

The optional securing member 70 made, for example, of cobalt-chrome alloy to ASTM F-799 specifications or to more or less demanding standards, and generally in the shape of a ring, includes ring body 72 with marginal arcs 74 and hood braces 75 that include bevel 75B, cover 75C, and perforations 75P, which may take the form of holes. Engagement tabs 76 are biased inwardly, and have edges 76E that may engage the material of the cup 50 about the hood 55 and side hole 55H, which may occur slightly above any lip 56, so as to help secure the ring 70 to the cup 50. In conjunction with or in lieu of the tabs 76 can be side holes 76H. Added fasteners 77 such as screws may be provided for further security, for example, which may be passed through the perforations and/or holes 75P, 76H.

The present invention is thus provided. Various feature(s), part(s), subcombination(s) and combination(s) may be employed with or without reference to other feature(s), part(s), subcombination(s) or combination(s) whereof, and numerous adaptations and modifications can be effected within its spirit, the literal claim scope of which is particularly pointed out as follows:

I claim:

1. A hard substance enarthrodial joint implant ensemble comprising a double-hooded articular cup of a first hard substance that is a first suitable biocompatible, rigid, hard, strong material; and an insert having a head of a second hard substance that is a second suitable biocompatible, rigid, hard, strong material with an articulation surface therefor—wherein:

the cup includes a head-receiving cup made of the first hard substance, which is adapted and configured to be fixed when implanted into a patient such that the cup is fixed with respect to the patient directly or with respect to a backing shell in which the cup resides when the backing shell is present and fixed directly to the patient, which has an articular surface upon which the articulation surface of the head can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the head when the head is inserted into the cup;

the insert includes a joint head made of the second hard substance, which has a head body configured generally in a shape of a truncated sphere; a generally spherical articulation surface on the head body; and a truncation to the head body forming a truncated surface in which resides a blind hole for receipt of a trunnion of a stem, wherein:

the truncated surface is at a central truncation distance extending from a peak of the spherical articulation surface to a center of the truncated surface, wherein the central truncation distance is perpendicular to the truncated surface; and the head can be inserted into and retained by the hard substance double-headed articular cup when the head is inserted into the cup;

the first and second hard substances are the same as or different from the other, with at least one of the first hard substance and the second hard substance being other than ceramic; and there is no securing member present for resistance against any likelihood of cracking, fracture, or other failure of the hard substance by application of outwardy displacing force on the hoods.

2. The implant ensemble of claim 1, which further comprises the stem having the trunnion, wherein the stem includes an elongate member for insertion into bone; and the trunnion has a male surface inserted into, registering with, and secured by the blind hole of the head.

3. The implant ensemble of claim 2, wherein the blind hole of the head of the insert is a frustoconical blind hole; the male surface of the trunnion is a frustoconical male surface configured to correspond with the frustoconical blind hole of the head of the insert and provide for a self-locking taper; and the enarthrodial joint is a hip joint.

4. The implant ensemble of claim 3, wherein the central truncation distance of the head is about from 60% to 85% of the head diameter.

5. The implant ensemble of claim 2, wherein the blind hole of the head of the insert is a frustoconical blind hole; the male surface of the trunnion is a frustoconical male surface configured to correspond with the frustoconical blind hole of the head of the insert and provide for a self-locking taper; and the enarthrodial joint is a shoulder joint.

6. The implant ensemble of claim 5, wherein the central truncation distance of the head is about from 60% to 85% of the head diameter.

7. The implant ensemble of claim 6, wherein at least one of the following features (A-G) is present:
(A) the frustoconical blind hole of the head has a Morse taper, and the frustoconical male surface of the trunnion has a corresponding Morse taper;
(B) any ceramic, when present, is MgO-TTZ;
(C) a circumferential outwardly facing groove around the cup, but not the hoods, into which a circumferential ring is positioned;
(D) an outer backing shell for the cup;
(E) a bone-interfacing coating;
(F) a non-magnetic cobalt-chromium molybdenum alloy as a wrought powder metallurgy product is employed to make at least one of the cup, the head, and the stem; and
(G) the margin and hoods are angled about from five to twenty degrees with respect to a line or plane perpendicular to a central axis of the cup.

8. The implant ensemble of claim 2, wherein the central truncation distance of the head is about from 60% to 85% of the head diameter.

9. The implant ensemble of claim 1, wherein the central truncation distance of the head is about from 60% to 85% of the head diameter.

10. The implant ensemble of claim 1, wherein both the first hard substance and the second hard substance are other than ceramic.

11. The implant ensemble of claim 1, which is a hip joint.

12. A hard substance double-hooded articular cup for an enarthrodial joint implant, which comprises a head-receiving cup made of a hard substance that is a suitable biocompatible, rigid, hard, strong material other than ceramic, which is adapted and configured to be fixed when implanted into a patient such that the cup is fixed with respect to the patient directly or with respect to a backing shell in which the cup resides when the backing shell is present and fixed directly to the patient, which has an articular surface upon which a head of a joint can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the head when the head is inserted into the cup, wherein there is no securing member present for resistance against any likelihood of cracking, fracture, or other failure of the hard substance by application of outwardly displacing force on the hoods.

13. The cup of claim 12, wherein the joint implant is a hip implant.

14. The cup of claim 12, wherein the joint implant is a shoulder implant.

15. The cup of claim 12, wherein the hard substance is a fiber reinforced polymer composite.

16. The cup of claim 12, wherein the hard substance is a metal or metal alloy.

17. The cup of claim 12, wherein the hard substance is a cobalt-chromium-molybdenum alloy.

18. A hard substance joint head for an enarthrodial joint implant having a hard substance double-hooded articular cup, which comprises a head body that is a suitable biocompatible, rigid, hard, strong material other than ceramic, configured generally in a shape of a truncated sphere; a generally spherical articulation surface on the head body; and a truncation to the head body forming a truncated surface in which resides a blind frustoconical hole for receipt of a trunnion of a stem, wherein the truncated surface is at a central truncation distance extending from a peak of the spherical articulation surface to a center of the truncated surface, wherein the central truncation distance is perpendicular to the truncated surface and is about from 60% to 85% of the head diameter; the joint head is configured for insertion into and retention by the hard substance double-hooded articular cup that is adapted and configured to be fixed when implanted into a patient such that the cup is fixed with respect to the patient directly or with respect to a backing shell in which the cup resides when the backing shell is present and fixed directly to the patient, which has an articular surface upon which the articulation surface of the joint head can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the joint head when the joint head is inserted into the cup, and wherein there is no securing member present for resistance against any likelihood of cracking, fracture, or other failure of the hard substance by application of outwardy displacing force on the hoods.

19. The head of claim 18, wherein the joint implant is a hip implant.

20. The head of claim 18, wherein the joint implant is a shoulder implant.

21. The head of claim 18, wherein the hard substance is a fiber reinforced polymer composite; and the central truncation distance is about from 65% to 80% of the head diameter.

22. The head of claim 18, wherein the hard substance is a metal or metal alloy; and the central truncation distance is about from 65% to 80% of the head diameter.

23. The head of claim 18, wherein the hard substance is a cobalt-chromium-molybdenum alloy; and the central truncation distance is about from 65% to 80% of the head diameter.

24. A hard substance enarthrodial joint implant device comprising at least one of A) a double-hooded articular cup of a first hard substance that is a first suitable biocompatible, rigid, hard, strong material; and B) an insert having a head of a second hard substance that is a second suitable biocompatible, rigid, hard, strong material with an articulation surface therefor—wherein;

the cup includes a head-receiving cup made of the first hard substance, which is adapted and configured to be fixed when implanted into a patient such that the cup is fixed with respect to the patient directly or with respect to a backing shell in which the cup resides when the backing shell is present and fixed directly to the patient, which has an articular surface upon which the articulation surface of the head can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the head when the head is inserted into the cup;

the insert includes a joint head made of the second hard substance, which has a head body configured generally in a shape of a truncated sphere; a generally spherical articulation surface on the head body; and a truncation to the head body forming a truncated surface in which resides a blind hole for receipt of a trunnion of a stem, wherein the truncated surface is at a central truncation distance extending from a peak of the spherical articulation surface to a center of the truncated surface, wherein the central truncation distance is perpendicular to the truncated surface; and the head can be inserted into and retained by the hard substance double-headed articular cup when the head is inserted into the cup;

the first and second hard substances are the same as or different from the other, with, at least one of the first and second hard substances being as follows:

in all enarthrodial joint applications, alumina, a silicon nitride ceramic, or a zirconia ceramic other than MgO-TTZ; and provided that the device is an enarthrodial joint component or ensemble other than that for a hip, MgO-TTZ; and there is no securing member present for resistance against any likelihood of cracking, fracture, or other failure of the hard substance by application of outwardy displacing force on the hoods.

25. The device of claim 24, wherein the central truncation distance of the head is about from 60% to 85% of the head diameter.

26. The device of claim 24, which includes both the cup and the insert as an ensemble.

27. The device of claim 24, wherein the hard substance is alumina.

28. The device of claim 24, which is for a shoulder.

29. The device of claim 24, which is for the hip.

30. The implant ensemble of claim 1, which is a shoulder joint.

* * * * *